United States Patent
Asai

(10) Patent No.: US 11,818,464 B2
(45) Date of Patent: Nov. 14, 2023

(54) MEDICAL IMAGE TRANSMISSION SYSTEM, MEDICAL IMAGE PROCESSING APPARATUS, AND MEDICAL IMAGE TRANSMISSION METHOD

(71) Applicant: Sony Group Corporation, Tokyo (JP)

(72) Inventor: Atsushi Asai, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 186 days.

(21) Appl. No.: 17/435,039

(22) PCT Filed: Mar. 24, 2020

(86) PCT No.: PCT/JP2020/012817
§ 371 (c)(1),
(2) Date: Aug. 31, 2021

(87) PCT Pub. No.: WO2020/206428
PCT Pub. Date: Oct. 8, 2020

(65) Prior Publication Data
US 2022/0141386 A1 May 5, 2022

(30) Foreign Application Priority Data
Mar. 29, 2019 (JP) .................. 2019-065974

(51) Int. Cl.
*H04N 23/68* (2023.01)
*A61B 1/00* (2006.01)
(Continued)

(52) U.S. Cl.
CPC ......... *H04N 23/683* (2023.01); *A61B 1/0005* (2013.01); *A61B 1/00006* (2013.01);
(Continued)

(58) Field of Classification Search
CPC .......... A61B 1/00006; A61B 1/000095; A61B 1/0005; A61B 1/00188; G06T 3/4038;
(Continued)

(56) References Cited

U.S. PATENT DOCUMENTS

2004/0061776 A1 4/2004 Mochida
2005/0020879 A1 1/2005 Suzuki
(Continued)

FOREIGN PATENT DOCUMENTS

JP 2000-287202 A 10/2000
JP 2002-112958 A 4/2002
(Continued)

OTHER PUBLICATIONS

International Search Report and Written Opinion dated Jun. 9, 2020, received for PCT Application PCT/JP2020/012817, Filed on Mar. 24, 2020, 9 pages including English Translation.

*Primary Examiner* — Antoinette T Spinks
(74) *Attorney, Agent, or Firm* — XSENSUS LLP

(57) ABSTRACT

[Object] To provide a medical image transmission system, a medical image processing apparatus, and a medical image transmission method that are capable of performing image processing on a medical image generated in a modality without deteriorating the visibility of additional information. [Solving Means] A medical image transmission system according to the present technology includes: an image acquisition unit; image processing unit; a superimposition unit; and a presentation unit. The image acquisition unit acquires a medical image generated by a medical observation apparatus. The image processing unit applies predetermined image processing to the medical image. The superimposition unit superimposes a superimposition image on a predetermined area of the medical image. The presentation unit presents information to a user on the basis of additional (Continued)

information that has been displayed in the predetermined area before executing the predetermined image processing. [Selected Drawing] FIG. 10

15 Claims, 16 Drawing Sheets

(51) Int. Cl.
*H04N 5/262* (2006.01)
*H04N 5/268* (2006.01)
*H04N 5/272* (2006.01)
*H04N 23/50* (2023.01)

(52) U.S. Cl.
CPC ......... *A61B 1/00188* (2013.01); *H04N 5/268* (2013.01); *H04N 5/2628* (2013.01); *H04N 5/272* (2013.01); *H04N 23/555* (2023.01); *H04N 23/6811* (2023.01)

(58) Field of Classification Search
CPC ............ H04N 23/555; H04N 23/6811; H04N 23/6812; H04N 23/683; H04N 5/2628; H04N 5/268; H04N 5/272; H04N 7/183; H04N 7/185

USPC ...................................................... 348/208.6
See application file for complete search history.

(56) References Cited

U.S. PATENT DOCUMENTS

| | | | | |
|---|---|---|---|---|
| 2019/0133711 A1* | 5/2019 | Wade | .................... | A61B 34/25 |
| 2022/0401049 A1* | 12/2022 | Terakado | ............... | A61B 1/043 |

FOREIGN PATENT DOCUMENTS

| | | |
|---|---|---|
| JP | 2004-335 A | 1/2004 |
| JP | 3650142 B2 | 5/2005 |
| JP | 2011-156262 A | 8/2011 |
| JP | 4813178 B2 | 11/2011 |
| JP | 2013-77075 A | 4/2013 |
| JP | 2017-170157 A | 9/2017 |
| JP | 2017-185254 A | 10/2017 |
| WO | 2010/041457 A1 | 4/2010 |

* cited by examiner

MEDICAL IMAGE TRANSMISSION SYSTEM, MEDICAL IMAGE PROCESSING APPARATUS, AND MEDICAL IMAGE TRANSMISSION METHOD

CROSS-REFERENCE TO RELATED APPLICATIONS

The present application is based on PCT filing PCT/JP2020/012817, filed Mar. 24, 2020, which claims priority to JP 2019-065974, filed Mar. 29, 2019, the entire contents of each are incorporated herein by reference.

TECHNICAL FIELD

The present technology relates to a medical image transmission system, a medical image processing apparatus, and a medical image transmission method according to image processing of a medical image generated by a medical observation apparatus.

BACKGROUND ART

In a modality (medical observation apparatus) such as an endoscope and a microscope, an image blur occurs when shaking such as camera shake and floor vibrations occurs. In particular, in recent years, as the modality becomes higher in definition, the effect of the image blur on visibility becomes larger.

Meanwhile, for example, in Patent Literature 1, an endoscope in which a gyro is provided in a camera head and camera shake is detected by the gyro and corrected in an output image has been proposed.

CITATION LIST

Patent Literature

Patent Literature 1: Japanese Patent Application Laid-open No. 2017-185254

DISCLOSURE OF INVENTION

Technical Problem

However, although it is sufficient that the camera shake correction function is mounted on a modality as described in Patent Literature 1, in the case where such a camera shake correction function is not mounted, the camera shake correction cannot be performed on the modality side.

In this case, image processing such as camera shake correction needs to be performed later on the image output from the modality. Here, additional information such as modality setting and character information indicating an alert is often superimposed on the image output from the modality. For this reason, when image processing such as camera shake correction is performed on such an image, the additional information is also subjected to image processing, which causes a problem that the visibility of the additional information is deteriorated.

In view of the circumstances as described above, it is an object of the present technology to provide a medical image transmission system, a medical image processing apparatus, and a medical image transmission method that are capable of performing image processing on a medical image generated in a modality without deteriorating the visibility of additional information.

Solution to Problem

In order to achieve the above-mentioned object, a medical image transmission system according to the present technology includes: an image acquisition unit; an image processing unit; a superimposition unit; and a presentation unit.

The image acquisition unit acquires a medical image generated by a medical observation apparatus.

The image processing unit applies predetermined image processing to the medical image.

The superimposition unit superimposes a superimposition image on a predetermined area of the medical image.

The presentation unit presents information to a user on the basis of additional information that has been displayed in the predetermined area before executing the predetermined image processing.

In order to achieve the above-mentioned object, a medical image processing apparatus according to the present technology includes: an image acquisition unit; an image processing unit; a superimposition unit; and a presentation unit.

The image acquisition unit acquires a medical image generated by a medical observation apparatus.

The image processing unit applies predetermined image processing to the medical image.

The superimposition unit superimposes a superimposition image on a predetermined area of the medical image.

The presentation unit generates a presentation image including the medical image on which the superimposition image has been superimposed by the superimposition unit and additional information that has been displayed in the predetermined area before executing the predetermined image processing.

In order to achieve the above-mentioned object, a medical image transmission method according to the present technology includes: acquiring, by an image acquisition unit, a medical image generated by a medical observation apparatus.

An image processing unit applies predetermined image processing to the medical image.

A superimposition unit superimposes a superimposition image on a predetermined area of the medical image.

A presentation unit presents information to a user on the basis of additional information that has been displayed in the predetermined area before executing the predetermined image processing.

In accordance with this configuration, a user can refer to both a medical image subjected to image processing and additional information.

MODE(S) FOR CARRYING OUT THE INVENTION

First Embodiment

A medical image transmission system according to a first embodiment of the present technology will be described.

[Configuration of Medical Image Transmission System]

Figure 1:
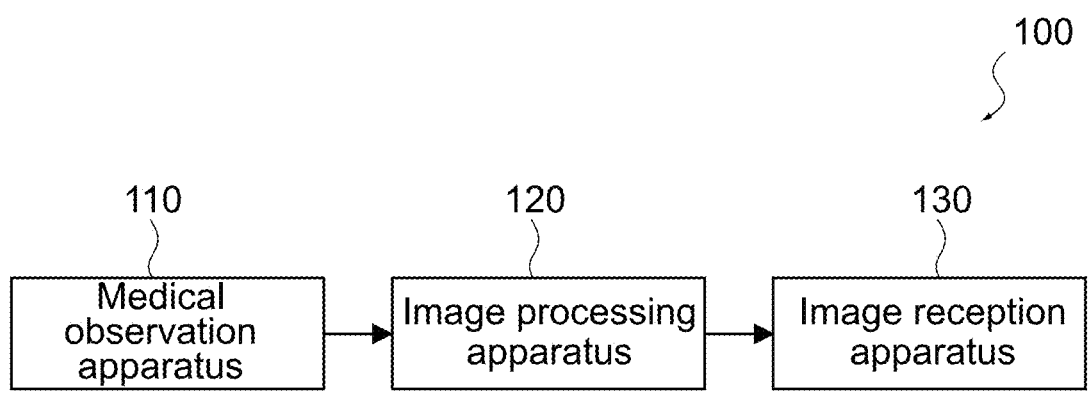
FIG. 1 is a block diagram showing a configuration of a medical image transmission system according to a first embodiment of the present technology.

FIG. 1 is a block diagram showing a configuration of a medical image transmission system 100 (hereinafter, the transmission system 100) according to this embodiment. As shown in the figure, the transmission system 100 includes a medical observation apparatus 110, an image processing apparatus 120, and an image reception apparatus 130.

The medical observation apparatus 110 and the image processing apparatus 120, and the image processing apparatus 120 and the image reception apparatus 130 are wired or wirelessly connected to each other.

The medical observation apparatus 110 images an imaging target and generates a medical image. The imaging target is not particularly limited, and is, for example, a biological tissue. The medical observation apparatus 110 only needs to be an apparatus having a function of capturing an image, such as an endoscope and a microscope, and the configuration thereof is not particularly limited. The medical observation apparatus 110 is called also as a modality.

The image processing apparatus 120 performs image processing described below on the medical image output from the medical observation apparatus 110, and generates a presentation image. Further, the image processing apparatus 120 outputs the generated presentation image to the image reception apparatus 130.

The image processing apparatus 120 only needs to be an apparatus capable of performing image processing such as camera shake correction on a medical image, and can be, for example, an IP (Interlace Protocol) converter that converts an electrical signal of an image into an optical signal. Further, the image processing apparatus 120 may be an information processing apparatus.

The image reception apparatus 130 receives the presentation image output from the image processing apparatus 120. The image reception apparatus 130 can be a display that displays a presentation image, a recorder that records a presentation image, an image management server, or the like.

[Specific Example of Medical Image Transmission System]

Figure 2:
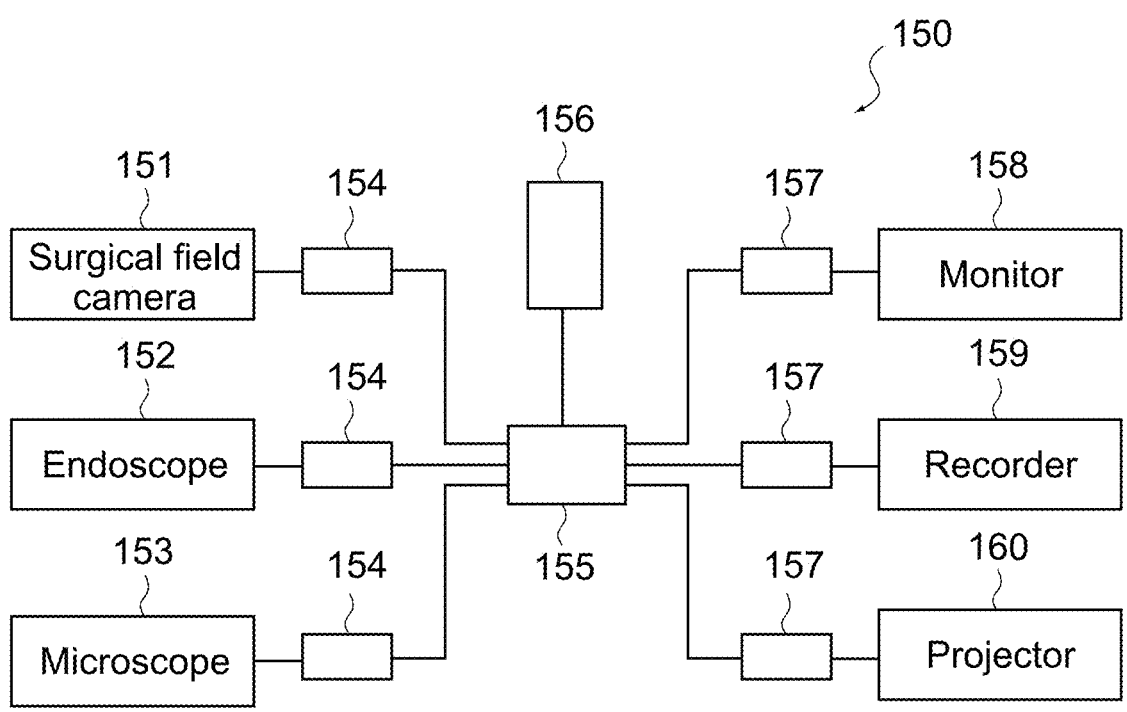
FIG. 2 is a schematic diagram showing a specific example of the medical image transmission system.

FIG. 2 is a schematic diagram showing a configuration of a medical image transmission system 150 (hereinafter, the transmission system 150) as a specific example of the transmission system 100. As shown in the figure, the transmission system 150 includes a surgical field camera 151, an endoscope 152, a microscope 153, IP converters 154, an optical switcher 155, a server 156, IP converters 157, a monitor 158, a recorder 159, and a projector 160.

The electrical signal of the medical image captured by each of the surgical field camera 151, the endoscope 152, and the microscope 153 is converted into an optical signal by the IP converter 154, and output to an arbitrary IP converter 157 by the optical switcher 155.

Each of the IP converters 157 converts the optical signal supplied from the optical switcher into an electrical signal, and supplies the electrical signal to the monitor 158, the recorder 159, or the projector 160. The server 156 instructs the optical switcher 155 about which IP converter 154 is to be connected to which IP converter 157.

The medical observation apparatus 110 shown in FIG. 1 corresponds to the surgical field camera 151, the endoscope 152, and the microscope 153, and the image reception apparatus 130 corresponds to the monitor 158, the recorder 159, and the projector 160. Further, the image reception apparatus 130 may be the server 156.

The image processing apparatus 120 corresponds to at least one of the IP converter 154, the IP converter 157, or the server 156. Note that the server 156 does not necessarily need to be provided in FIG. 2. In this case, the image processing apparatus 120 corresponds to at least one of the IP converter 154 or the IP converter 157.

Note that the specific configuration of the transmission system 150 shown in FIG. 2 is an example of the transmission system 100, and the transmission system 100 may be one in which the configuration shown in FIG. 1 is realized.

[Regarding Medical Image]

The medical observation apparatus 110 images an imaging target to generate an image, and generates a medical image on the basis of the image. Note that the "image" in the present disclosure may be a still image or a moving image.

Figure 3:
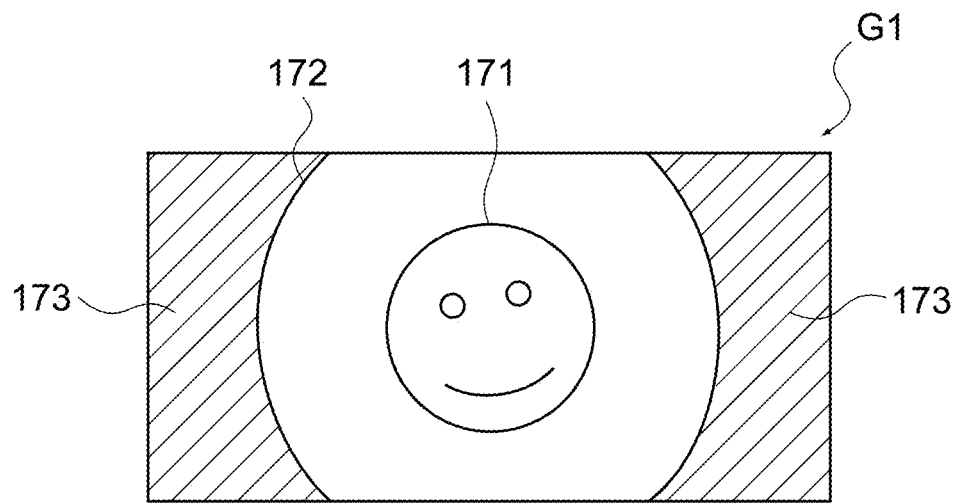
FIG. 3 is an example of a medical image (at the time of imaging) generated by a medical observation apparatus in the medical image transmission system.

FIG. 3 is an example of an image G1 generated by the medical observation apparatus 110. The image G1 is an unprocessed image generated by imaging an imaging target. As shown in the figure, the image includes an image 171 of an imaging target, an optical mask boundary 172, and an optical mask area 173.

The optical mask boundary 172 is the periphery of an optical field of view of an endoscope or the like. The optical mask area 173 that is an outer peripheral area of the optical mask boundary 172 is, for example, an area in which the inner periphery of the endoscope is imaged, and is an area filled with black or the like. Note that the image G1 does not necessarily need to include the optical mask boundary 172 and the optical mask area 173.

Figure 4:
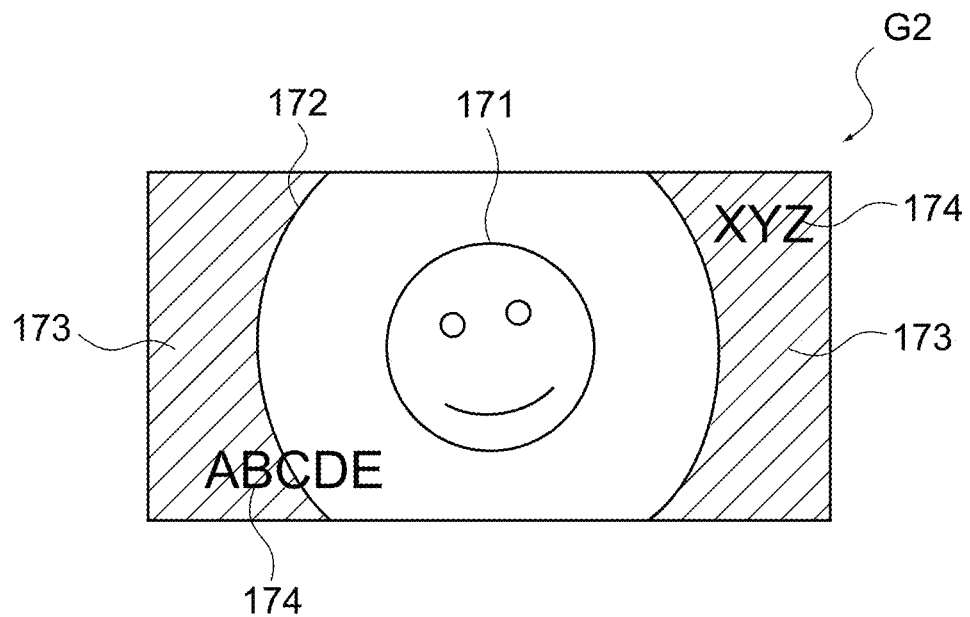
FIG. 4 is an example of a medical image (including additional information) generated by the medical observation apparatus in the medical image transmission system.

The medical observation apparatus 110 adds additional information to this image G1 to generate a medical image. FIG. 4 is an example of a medical image G2 generated by the medical observation apparatus 110. As shown in the figure, additional information 174 is added to the medical image G2.

The additional information 174 is, for example, character information such as the magnification of an endoscope, error display, and an alert, and can be a character string superimposed on the image G1. Further, the additional information is not limited to a character string, and may be an icon or the like. The medical observation apparatus 110 places the additional information 174 mainly on the optical mask area 173 so as not to interfere with the visual recognition of the image 171.

If camera shake correction is performed by the medical observation apparatus 110, it only needs to detect shaking of an imaging mechanism by a gyro or the like and perform correction for canceling the shaking by image processing. The medical observation apparatus 110 can place additional information on the image G1 after performing camera shake correction.

Meanwhile, in the case where camera shake correction is performed on the medical image G2 output from the medical observation apparatus 110 by an apparatus such as an IP converter other than the medical observation apparatus 110, a detection result of camera sake by a gyro or the like cannot be used. In this case, the camera shake can be corrected by executing processing of extracting a motion vector on the medical image G2 and moving the medical image G2 in opposite phase to the extracted motion vector.

Figure 5:
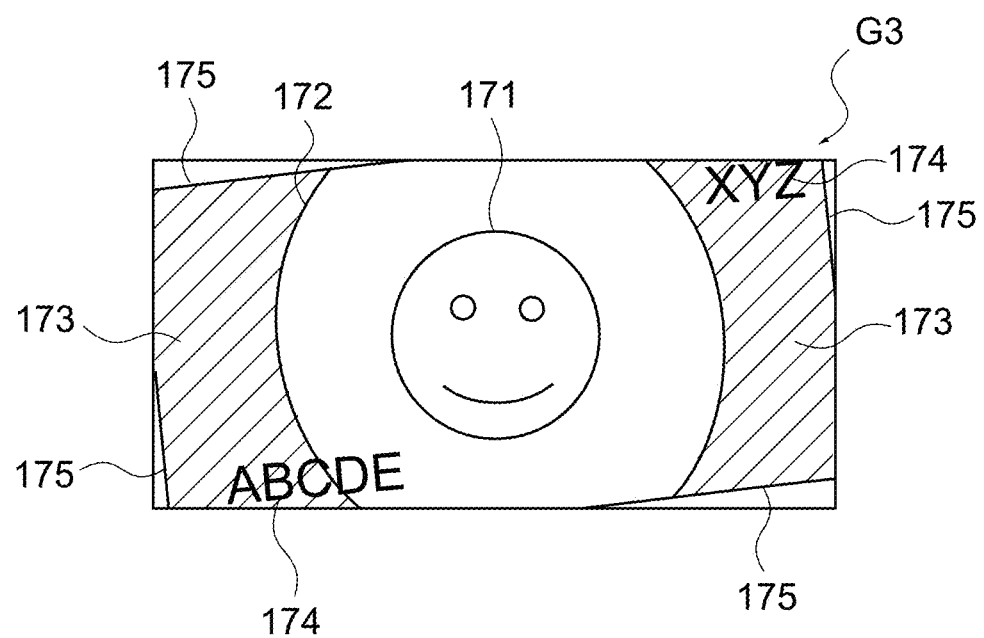
FIG. 5 is an example of a result of image processing in the medical image transmission system.

However, in this case, the following problem occurs. FIG. 5 is an example of a medical image G3 on which camera shake correction has been performed on the basis of the processing of extracting a motion vector.

As shown in the figure, although shaking of the image 171 is eliminated, the optical mask boundary 172, the additional information 174, and periphery 175 of the medical image G2 are shaken by, for example, moving/rotating the medical image G2 in order to suppress the shaking of the image 171, and the visibility of the medical image G3 is deteriorated. As a result, in the case where the medical image G3 is referred to perform a medical treatment or the like, there is a possibility that concentration of a user is reduced.

Figure 6:
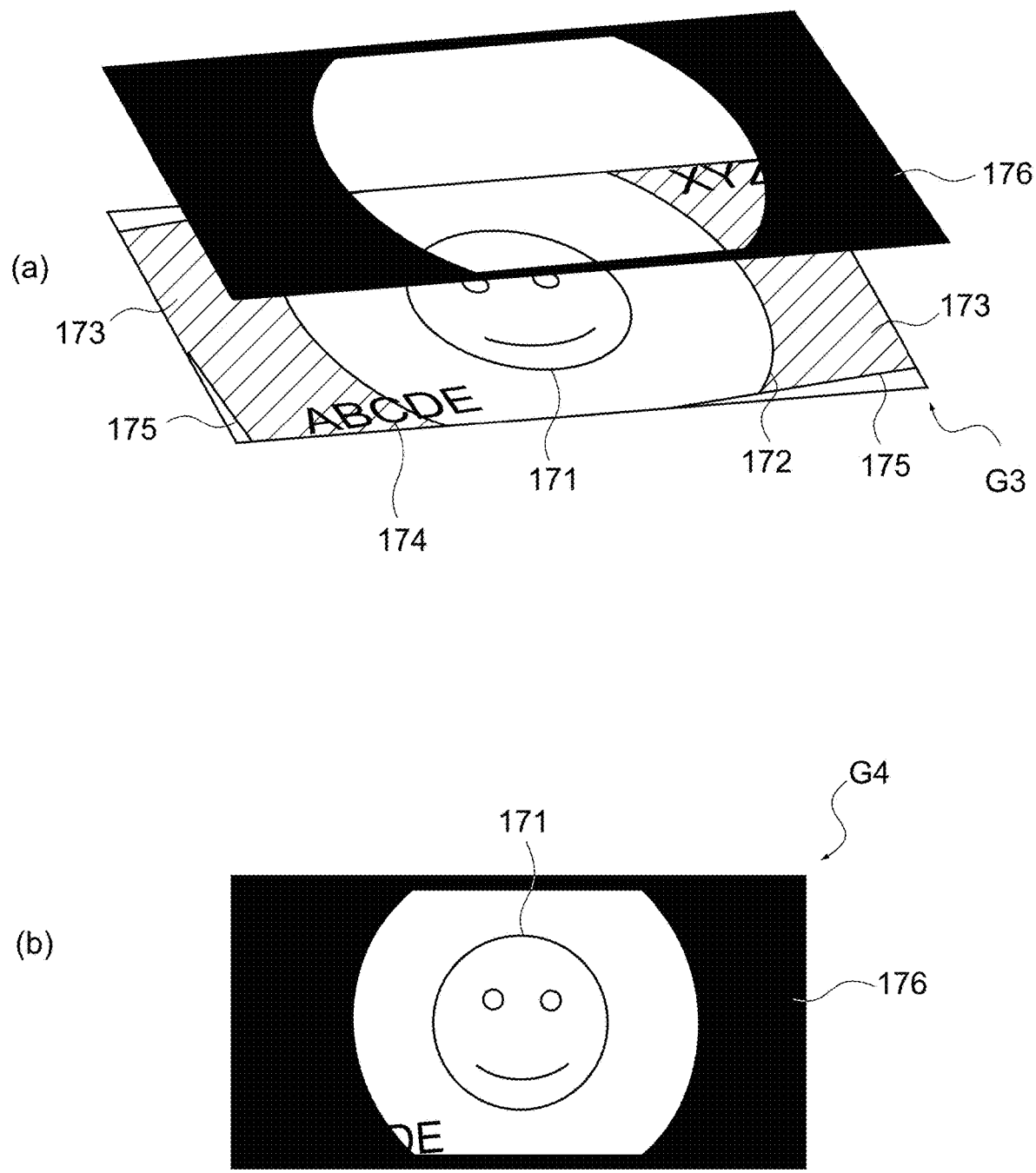
FIG. 6 is a schematic diagram showing how a superimposition image is superimposed in the medical image transmission system.

Meanwhile, a digital mask can be superimposed on the medical image G3. FIG. 6 is a schematic diagram showing how a digital mask is superimposed on the medical image G3. By superimposing a digital mask 176 covering areas other than the image 171 on the medical image G3 as shown in Part (a) of FIG. 6, the optical mask boundary 172, the additional information 174, and the periphery 175 can be covered by the digital mask 176 to obtain a medical image G4 as shown in Part (b) of FIG. 6.

As a result, it is possible to prevent the visibility due to shaking motion of the optical mask boundary 172 or the like from being deteriorated. However, since also the additional information 174 is covered by the digital mask 176, in the case where the additional information 174 is important information such as an alert and error presentation, the important information is not presented to a user and the user cannot grasp the important information.

Meanwhile, in the transmission system 100 according to this embodiment, these problem can be solved. Note that although camera shake correction has been described above as an example, the present technology is not limited to camera shake correction and is similarly applicable also to the case where an image is enlarged by digital zooming or the case where rotational correction is performed on an image.

Figure 7:
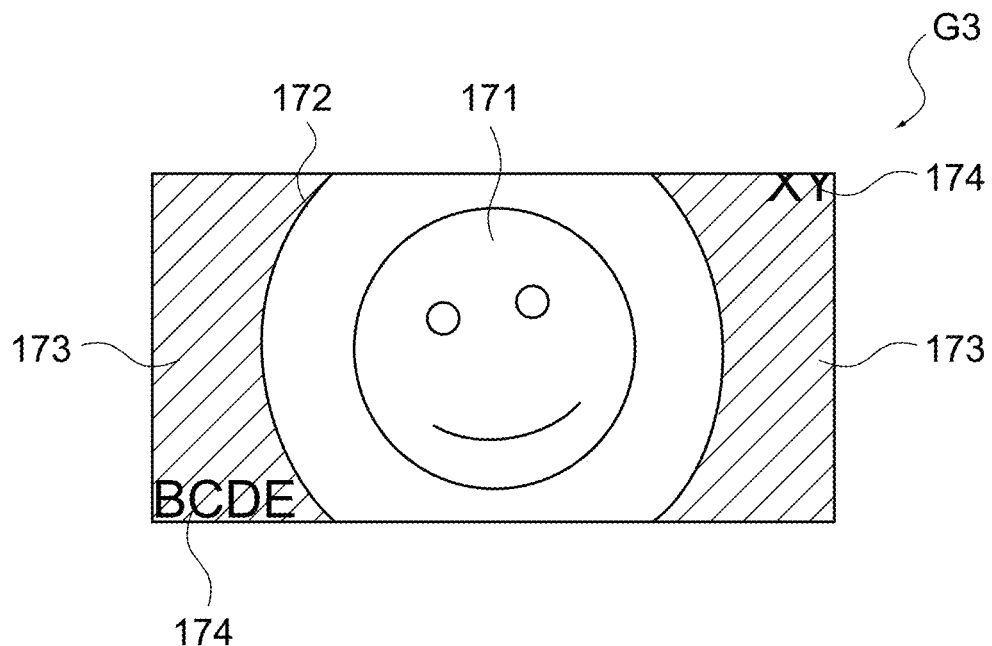
FIG. 7 is an example of a result of image processing in the medical image transmission system.
Figure 8:
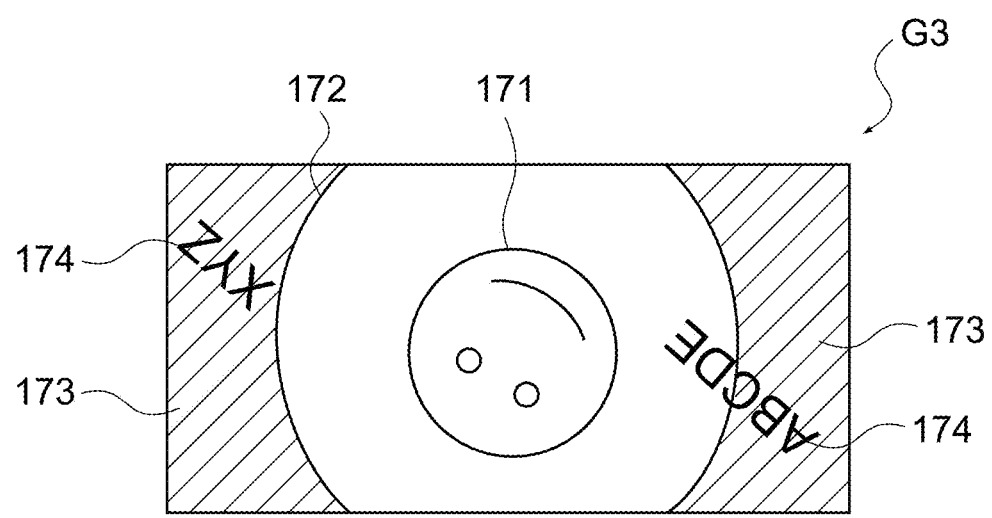
FIG. 8 is an example of a result of image processing in the medical image transmission system.

FIG. 7 is a schematic diagram showing the medical image G3 on which digital zooming has been performed on the medical image G2, and FIG. 8 is a schematic diagram showing the medical image G3 obtained by performing rotational correction on the medical image G2. In both cases, the visibility of the additional information 174 is deteriorated because the additional information 174 is not drawn or rotates.

[Regarding Configuration of Image Processing Apparatus]

Figure 9:
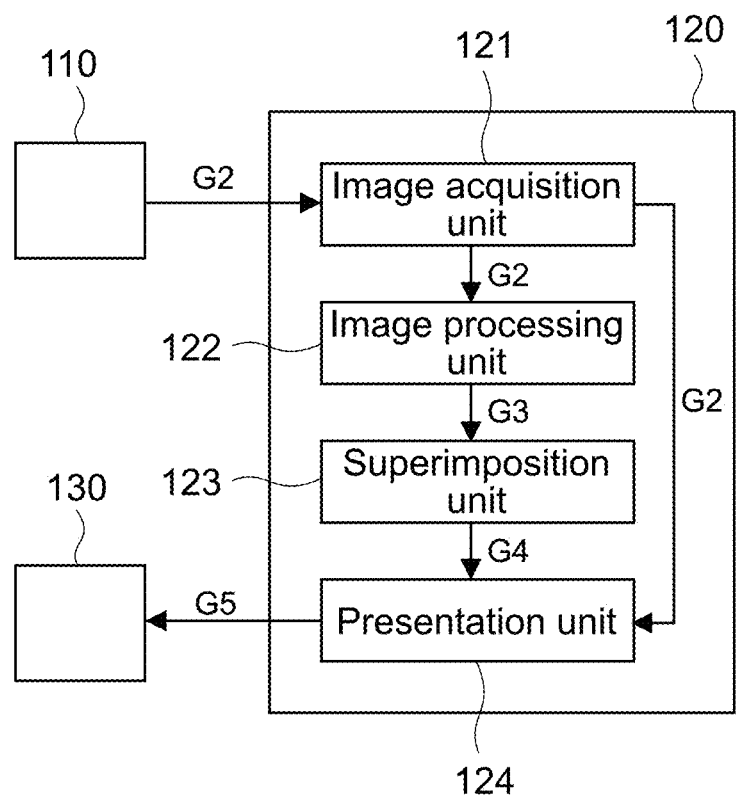
FIG. 9 is a block diagram showing a configuration of an image processing apparatus included in the medical image transmission system.

The configuration of the image processing apparatus 120 will be described. FIG. 9 is a schematic diagram showing a functional configuration of the image processing apparatus 120.

As shown in the figure, the image processing apparatus 120 includes an image acquisition unit 121, an image processing unit 122, a superimposition unit 123, and a presentation unit 124. These are functional configurations realized by the cooperation of software and hardware.

The image acquisition unit 121 acquires the medical image G2 (see FIG. 4) from the medical observation apparatus 110, and supplies it to the image processing unit 122 and the presentation unit 124.

The image processing unit 122 applies image processing to the medical image G2. The image processing is, for example, camera shake correction. The image processing unit 122 performs processing of extracting a motion vector on the medical image G2 and moves the medical image G2 in opposite phase to the extracted motion vector to perform camera shake correction. The image processing unit 122 supplies, to the superimposition unit 123, the medical image G3 (see FIG. 5) obtained by performing camera shake correction on the medical image G2.

The superimposition unit 123 superimposes a superimposition image on a predetermined area of the medical image G3. The superimposition image can be a digital mask that covers areas other than the image 171 in the medical image G3. As shown in FIG. 6, the superimposition unit 123 superimposes the digital mask 176 on the area of the medical image G3 to generate the medical image G4.

In the medical image G4, the regions of the medical image G3, which deteriorates the visibility, i.e., the optical mask boundary 172, the additional information 174, and the periphery 175 that cause shaking motion due to the image processing are covered by the digital mask 176. The superimposition unit 123 supplies the generated medical image G4 to the presentation unit 124.

The presentation unit 124 presents information to a user on the basis of the additional information 174 that has been displayed on the optical mask area 173 before performing the image processing by the image processing unit 122. Specifically, the presentation unit 124 generates a presentation image in which both the medical image G4 and the medical image G2 are respectively disposed as a main image and a sub-image in a picture-in-picture manner.

Figure 10:
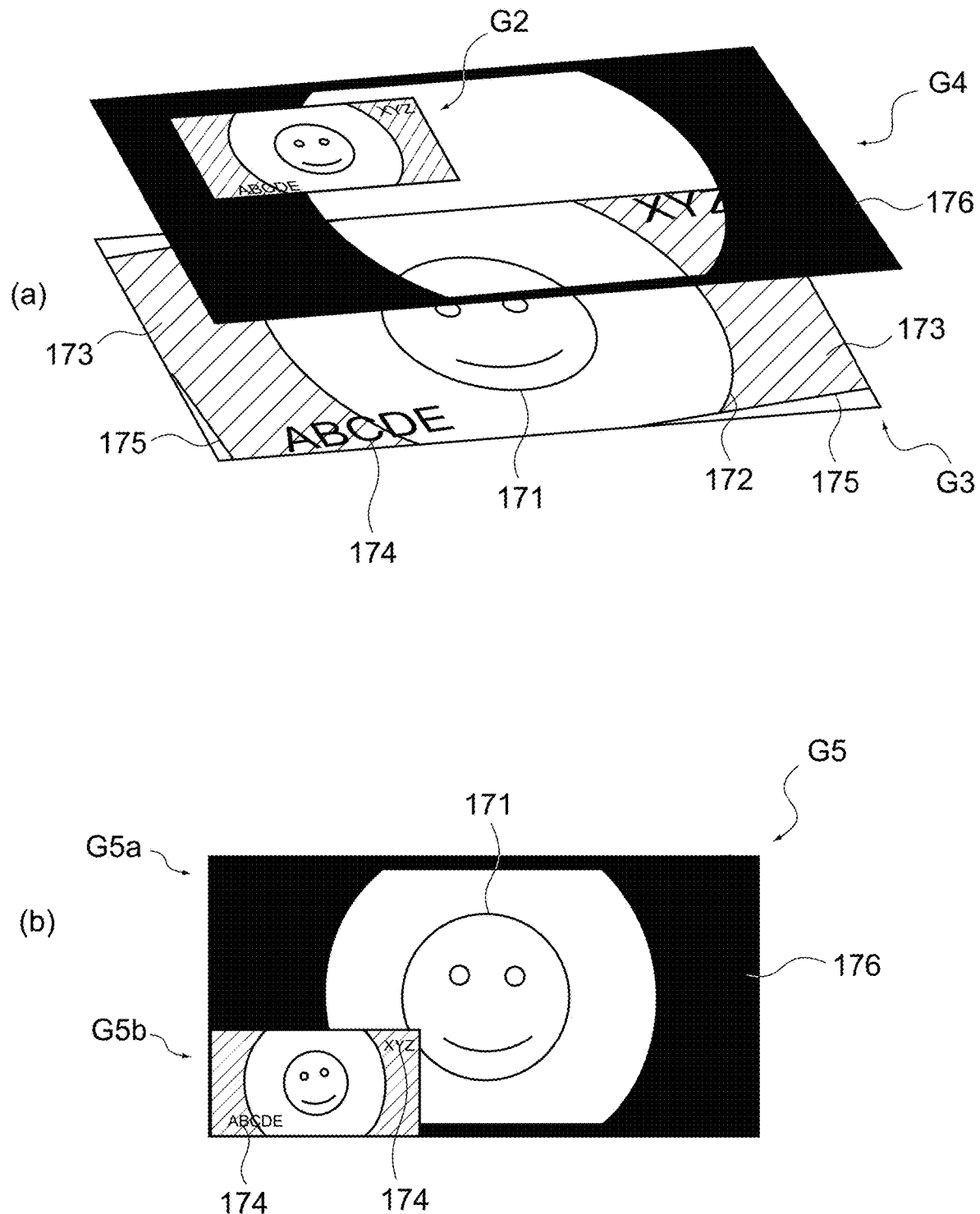
FIG. 10 is a schematic diagram showing a method of generating a presentation image by a presentation unit of the image processing apparatus included in the medical image transmission system.

FIG. 10 is a schematic diagram showing a method of generating a presentation image G5. As shown in Part (a) of FIG. 10, the presentation unit 124 downsizes the medical image G2 and superimposes the obtained image on the medical image G4 (the medical image G3 and the digital mask 176).

As a result, as shown in Part (b) of FIG. 10, the presentation image G5 in which the medical image G4 and the medical image G2 are respectively disposed as a main image G5a and a sub-image G5b in a picture-in-picture manner is generated. The medical image G2 includes the additional information 174 added by the medical observation apparatus 110 without change because the medical image G2 is an image before the image processing by the image processing unit 122 is performed. The presentation unit 124 outputs the generated presentation image G5 to the image reception apparatus 130.

[Effects by Medical Image Transmission System]

As described above, in the transmission system 100, the image processing apparatus 120 performs various types of processing on the medical image G2 (see FIG. 4) output from the medical observation apparatus 110 to generate the presentation image G5 (see FIG. 10), an outputs the generated image to the image reception apparatus 130.

In the presentation image G5, image processing such as camera shake correction is performed on the image 171 included in the main image G5a, and the digital mask 176 is superimposed on the periphery of the image 171. Therefore, the optical mask boundary 172, the additional information 174, and the periphery 175 are covered by the digital mask 176, and the visibility is prevented from being deteriorated due to the shaking thereof.

Further, the medical image G2 before image processing is disposed as the sub-image G5b in a picture-in-picture manner in the presentation image G5, and the additional information 174 can be checked. The additional information 174 in the medical image G2 is excellent in visibility because shaking motion due to camera shake correction has not occurred. As a result, a user can refer to both the medical image on which image processing has been performed and additional information that is not affected by the image processing.

Further, since only one monitor is necessary to display the presentation image G5, the increase in cost and installation location can be reduced and it does not take time and effort for setting, as compared with the case where the medical image G2 and the medical image G3 are displayed on a plurality of monitors.

[Regarding Another Configuration of Image Processing Apparatus]

The configuration of the image processing apparatus 120 is not limited to the one described above, and may have the following configuration.

For example, the image processing apparatus 120 may link the display/non-display of the digital mask 176 with the display/non-display of the sub-image G5b in a picture-in-picture manner.

The superimposition unit 123 may receive a predetermined operation input to superimpose the digital mask 176 on the medical image G3, and the presentation unit 124 may receive the operation input to dispose the sub-image G5b, thereby generating the presentation image G5.

As a result, the presentation unit 124 may output the medical image G3 to the image reception apparatus 130 until receiving the operation input, and output, when receiving the operation input, the presentation image G5 to the image reception apparatus 130. That is, a user can link the display/non-display of the digital mask 176 with the display/non-display of the sub-image G5b in a picture-in-picture manner by a single operation input.

Figure 11:
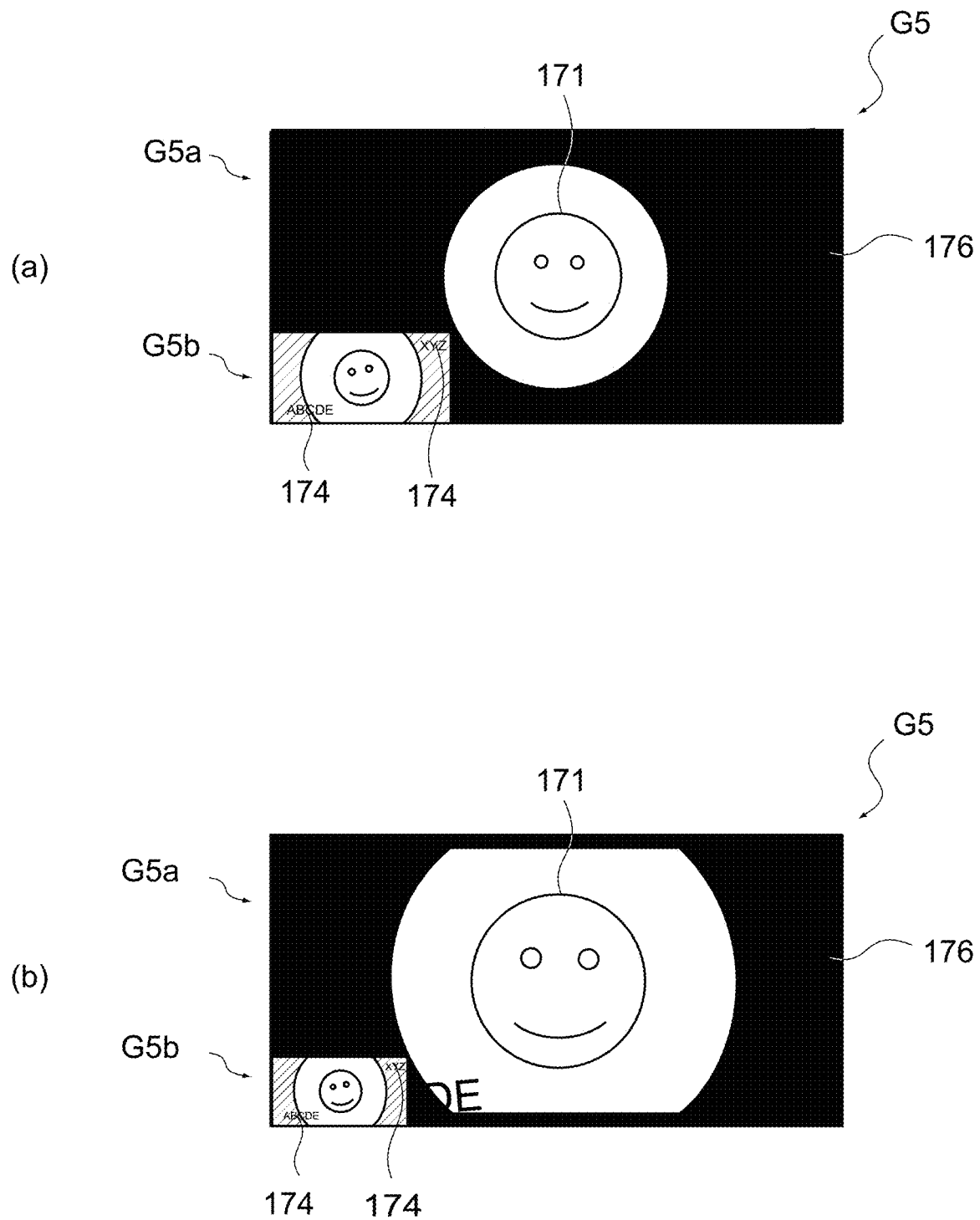
FIG. 11 is an example of a presentation image generated by the presentation unit of the image processing apparatus included in the medical image transmission system.

Further, the image processing apparatus 120 may adjust the image size of the sub-image G5b in the presentation image G5 in accordance with the size of the digital mask 176. FIG. 11 is a schematic diagram showing the adjustment of the size of the sub-image G5b.

As shown in Part (a) of FIG. 11, the presentation unit 124 increases the size of the sub-image G5b in the case where the size (width from the periphery of the image) of the digital mask 176 is large. Further, as shown in Part (b) of FIG. 11, the presentation unit 124 decreases the size of the sub-image G5b in the case where the size of the digital mask 176 is small. As a result, it is possible to prevent the sub-image G5b from being disposed inside the digital mask 176 in which the image 171 is present.

Figure 12:
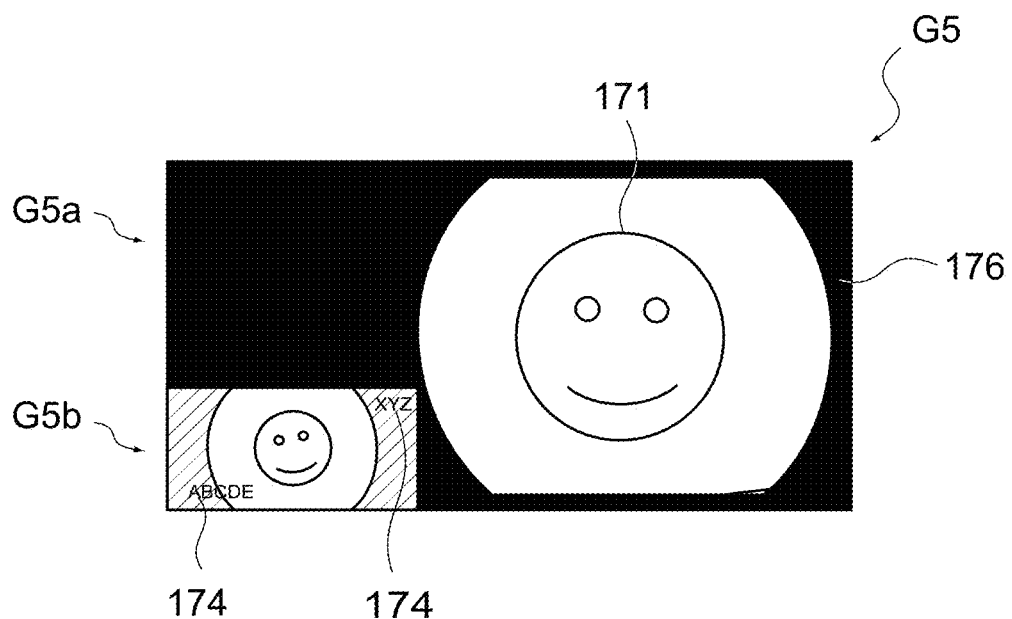
FIG. 12 is an example of a presentation image generated by the presentation unit of the image processing apparatus included in the medical image transmission system.

Further, the image processing apparatus 120 may offset the medical image G3 obtained by performing image processing on the medical image G2 output from the medical observation apparatus 110. FIG. 12 is a schematic diagram showing the presentation image G5 based on the offset medical image G3.

The image processing unit 122 may perform image processing on the medical image G2 and offset the medical image G2 to the right or left. As a result, the presentation unit 124 is capable of making the sub-image G5b larger on the digital mask 176.

Figure 13:
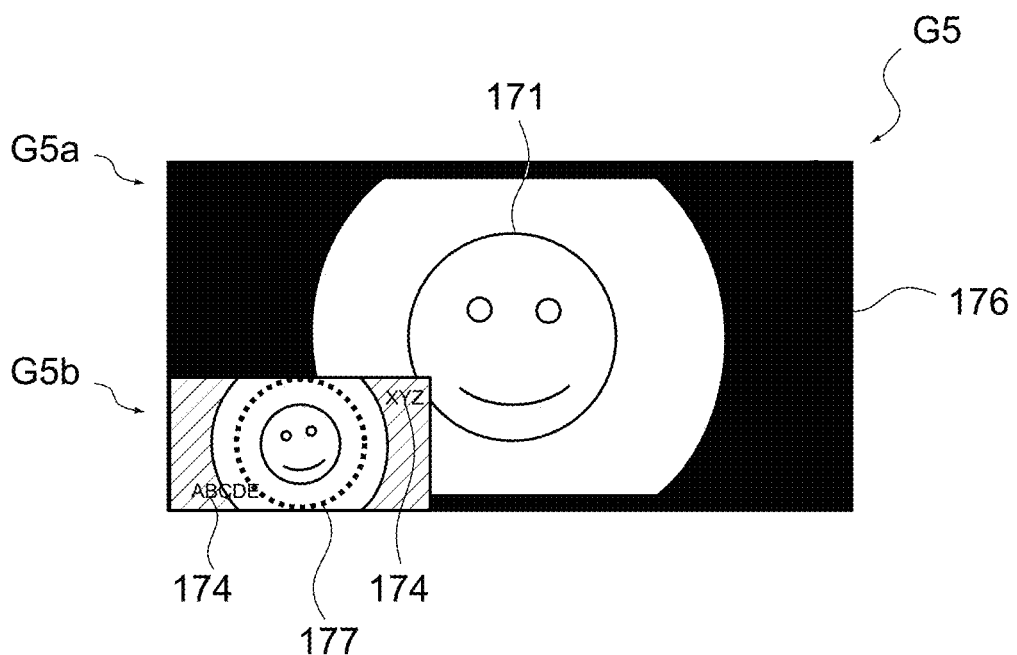
FIG. 13 is an example of a presentation image generated by the presentation unit of the image processing apparatus included in the medical image transmission system.

Further, the image processing apparatus 120 may dispose a display item indicating the range of the digital mask 176 on the sub-image G5b. FIG. 13 is a schematic diagram showing the presentation image G5 in which an outline 177 indicating the range of the digital mask 176 is disposed.

As shown in the figure, the presentation unit 124 may dispose the outline 177 indicating the range of the digital mask 176 on the sub-image G5b, and a user can adjust the position and size of the outline 177 by a predetermined operation input.

The superimposition unit 123 disposes the digital mask 176 such that the range specified by the outline 177 is the boundary of the digital mask 176. The digital mask 176 needs to be disposed such that the optical mask boundary 172 is hidden. When a user manually performs this setting, it is difficult to appropriately set the size of the digital mask 176 because the digital mask 176 covers the optical mask area 173.

In this regard, the image processing apparatus 120 disposes the outline 177 on the sub-image G5b, and thus, a user can easily grasp the positional relationship between the digital mask 176 and the optical mask area 173, and can easily adjust the position and size of the digital mask 176.

Note that the display item indicating the range of the digital mask 176 is not limited to the outline 177 and may be an arbitrary one as long as the range of the digital mask 176 can be grasped, such as changing the color of the area covered by the digital mask 176.

Figure 14:
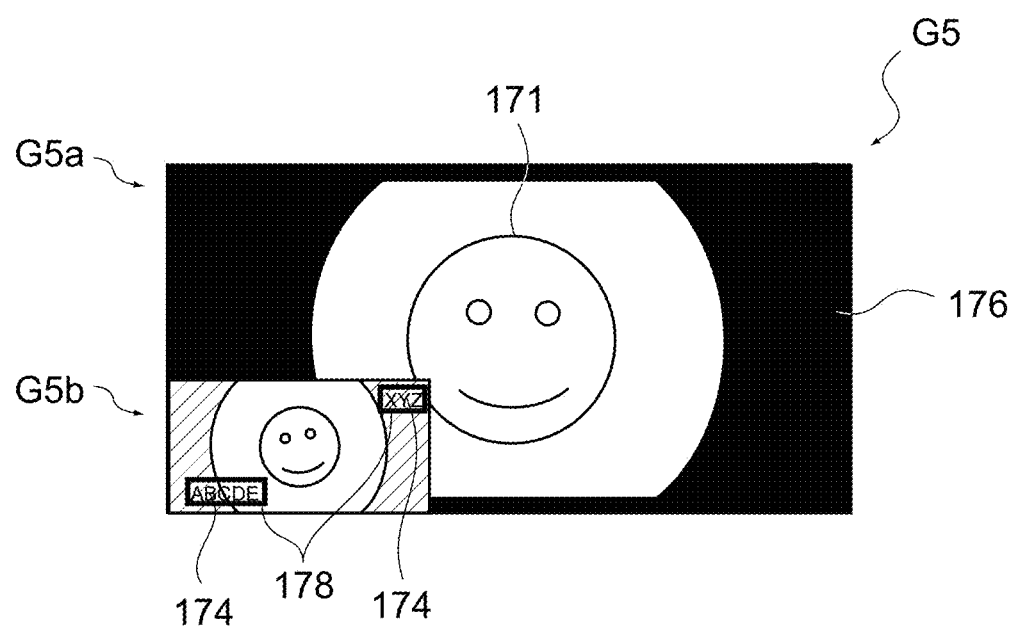
FIG. 14 is an example of a presentation image generated by the presentation unit of the image processing apparatus included in the medical image transmission system.

Further, the image processing apparatus 120 may perform processing of emphasizing the additional information 174 in the sub-image G5b. FIG. 14 is a schematic diagram showing the state in which the additional information 174 is emphasized in the sub-image G5b.

The presentation unit 124 executes image recognition on the sub-image G5b and extracts the additional information 174. Further, as shown in FIG. 14, the presentation unit 124 disposes a frame 178 surrounding the additional information 174 extracted in the sub-image G5b.

Since the medical image G2 is downsized in the sub-image G5b, the size of the additional information 174 is also reduced. By emphasizing the additional information 174 with the frame 178, it is possible to improve the visibility. Note that the presentation unit 124 may emphasize the additional information 174 by processing such as enlarging the extracted the additional information 174 and changing the color, in addition to the frame 178.

Figure 15:
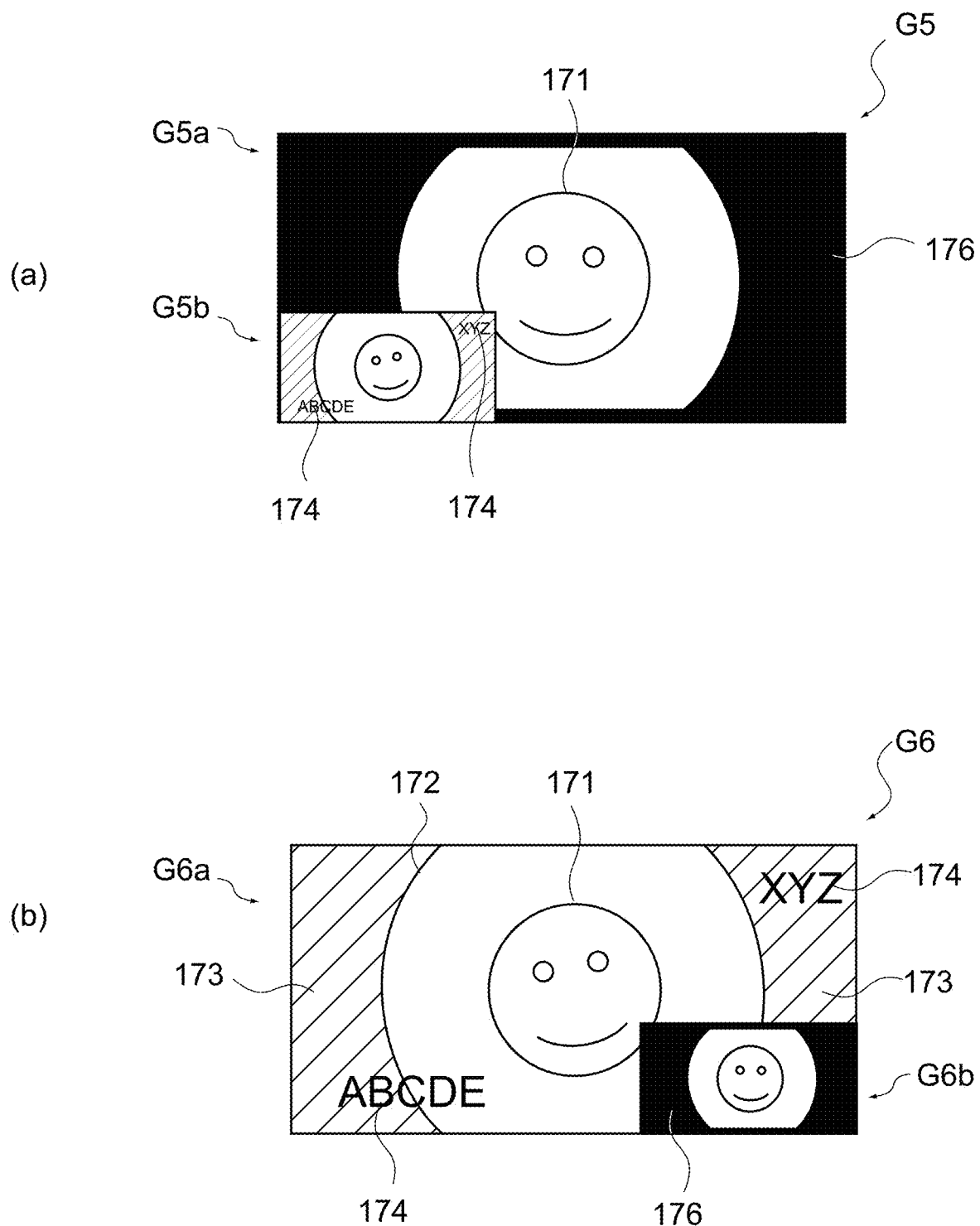
FIG. 15 is an example of a presentation image generated by the presentation unit of the image processing apparatus included in the medical image transmission system.

Further, the image processing apparatus 120 may be capable of switching between the main image G5a and the sub-image G5b in the presentation image G5. FIG. 15 is a schematic diagram showing how the main image G5a and the sub-image G5b are switched.

As described above, the presentation unit 124 generates the presentation image G5 in which the medical image G4 and the medical image G2 are respectively disposed as the main image G5a and the sub-image G5b in a picture-in-picture manner as shown in Part (a) of FIG. 15. Hereinafter, this state is referred to as the "first state".

Further, as shown in Part (b) of FIG. 15, the presentation unit 124 generates a presentation image G6 in which the medical image G2 and the medical image G4 are respectively disposed as a main image G6a and a sub-image G6b in a picture-in-picture manner. Hereinafter, this state is referred to as the "second state".

The presentation unit 124 may switch between the first state and the second state by receiving an operation input from a user. For example, during a medical treatment, a user desires to temporarily stop camera shake correction to check the content of the additional information 174 with a large image in some cases.

In such a case, as shown in FIG. 15, by enabling switching between the relationship between the main image and the sub-image of the medical image G2 and the medical image G4 by a single operation input, it is easy to switch from the first state to the second state and check the content of the additional information 174 with a large image.

Note that in the second state, in order to prevent the sub-image G6b from hiding the additional information 174 of the main image G6a, it is favorable to arbitrarily switch the position of the sub-image G6b. Although the sub-image G6b is disposed at the lower right of the presentation image G6 in FIG. 15, the sub-image G6b can be disposed in accordance with the position of the additional information 174, e.g., at one of four corners of the presentation image G6.

[Regarding Image Processing]

In the above-mentioned image processing by the image processing unit 122, presentation of additional information with a sub-image is performed because camera shake correction is performed on the medical image G2 and shaking motion of the additional information 174 or the like occurs (see FIG. 5).

Here, the image processing performed by the image processing unit 122 is not limited to camera shake correction, and may be zooming as shown in FIG. 7 or rotation as shown in FIG. 8. Also in these cases, the visibility of the additional information 174 in the medical image G3 is affected by the image processing, but it is possible to improve the visibility of the additional information 174 by generating the presentation image G5.

[Hardware Configuration]

Figure 16:
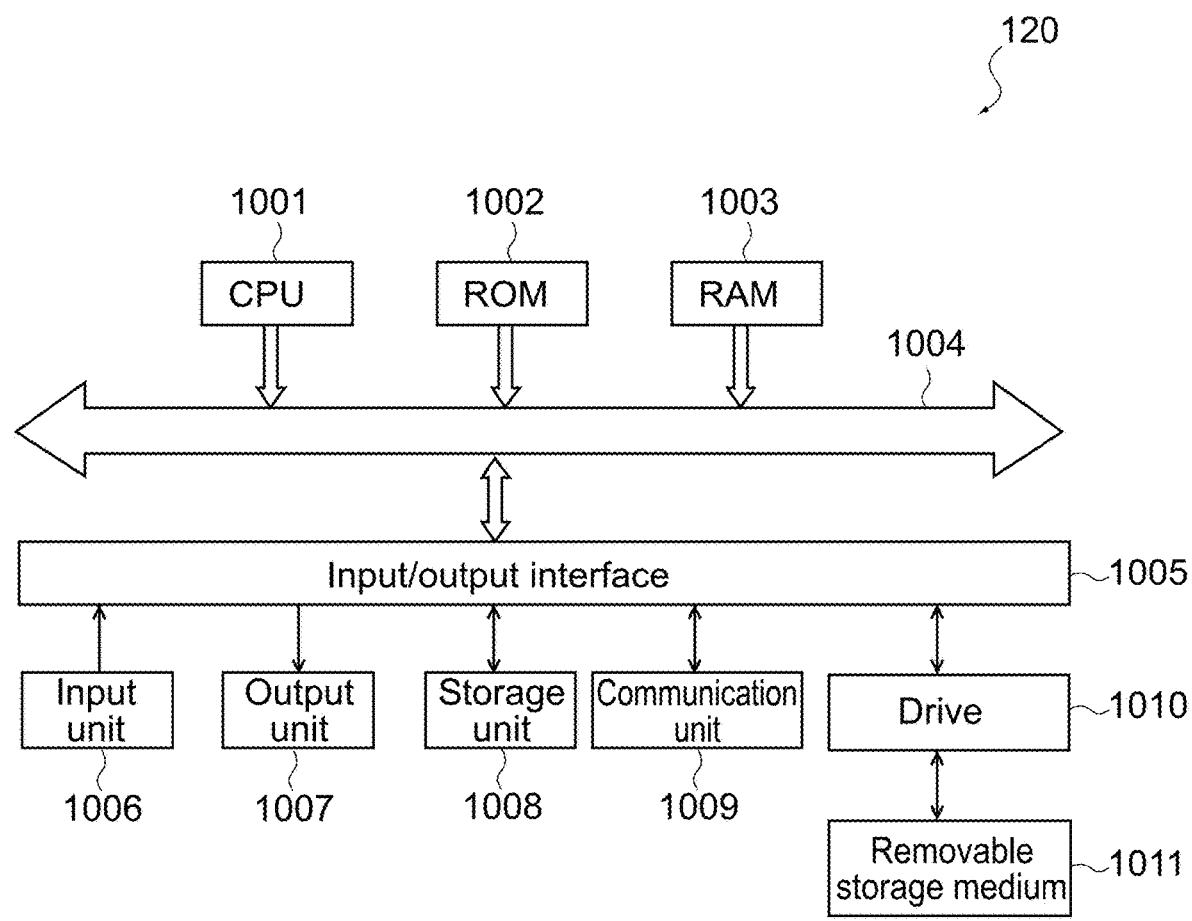
FIG. 16 is a block diagram showing a hardware configuration of the image processing apparatus included in the medical image transmission system.

The hardware configuration of the image processing apparatus 120 will be described. FIG. 16 is a schematic diagram showing a hardware configuration of the image processing apparatus 120.

As shown in the figure, the image processing apparatus 120 incorporates a CPU (Central Processing Unit) 1001. An input/output interface 1005 is connected to the CPU 1001 via a bus 1004. A ROM (Read Only Memory) 1002 and a RAM (Random Access Memory) 1003 are connected to the bus 1004.

An input unit 1006 that includes an input device such as a keyboard and a mouse for a user to input an operation command, an output unit 1007 that outputs an image of a processing operation screen and a processing result to a display device, a storage unit 1008 that includes a hard disk drive or the like storing a program and various types of data, and a communication unit 1009 that includes a LAN (Local Area Network) adapter or the like and executes communication processing via a network represented by the Internet are connected to the input/output interface 1005. Further, a drive 1010 that reads and writes data to/from a removable storage medium 1011 such as a magnetic disk, an optical disk, a magneto-optical disk, and a semiconductor memory is connected to the input/output interface 1005.

The CPU 1001 executes various types of processing in accordance with a program stored in the ROM 1002 or a program that is read from the removable storage medium 1011 such as a magnetic disk, an optical disk, a magneto-optical disk, and a semiconductor memory, installed in the storage unit 1008, and loaded from the storage unit 1008 into the RAM 1003. Data necessary for the CPU 1001 to execute various types of processing, and the like are appropriately stored in the RAM 1003.

In the image processing apparatus 120 configured as described above, the CPU 1001 loads, for example, the program stored in the storage unit 1008 into the RAM 1003 via the input/output interface 1005 and the bus 1004 and executes the program, whereby the above-mentioned series of processing is executed.

The program executed by the image processing apparatus 120 can be recorded on the removable storage medium 1011 as a package medium or the like and provided. Further, the program can be provided via a wired or wireless transmission medium such as a local area network, the Internet, and digital satellite broadcasting.

In the image processing apparatus 120, the program can be installed in the storage unit 1008 via the input/output interface 1005 by mounting the removable storage medium 1011 on the drive 1010. Further, the program can be received by the communication unit 1009 via a wired or wireless transmission medium and installed in the storage unit 1008. In addition, the program can be installed in the ROM 1002 or the storage unit 1008 in advance.

Note that the program executed by the image processing apparatus 120 may be a program that performs processing in time series in the order described in the present disclosure, or may be a program that performs processing in parallel or at necessary timings such as when a call is made.

Further, all of the hardware configurations of the image processing apparatus 120 need not be mounted on one device, and the image processing apparatus 120 may be configured by a plurality of devices. Further, a part of the hardware configurations of the image processing apparatus 120 may be mounted on a plurality of devices connected via a network. Further, the circuit that realizes the function of the image processing apparatus 120 may be a logical circuit such as FPGA (field-programmable gate array).

Second Embodiment

A medical image transmission system according to a second embodiment of the present technology will be described.

[Configuration of Medical Image Transmission System]

Figure 17:
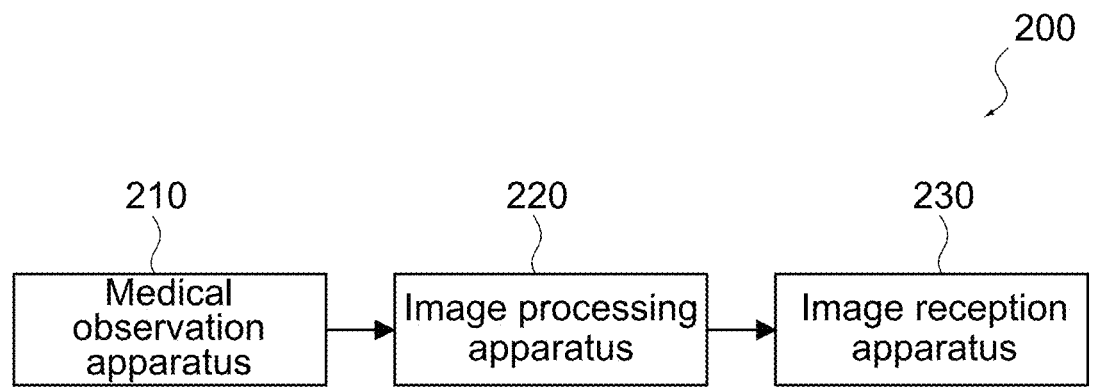
FIG. 17 is a block diagram showing a configuration of a medical image transmission system according to a second embodiment of the present technology.

FIG. 17 is a block diagram showing a configuration of a medical image transmission system 200 (hereinafter, the transmission system 200) according to this embodiment. As shown in the figure, the transmission system 200 includes a medical observation apparatus 210, an image processing apparatus 220, and an image reception apparatus 230.

The medical observation apparatus 210 and the image processing apparatus 220, and the image processing apparatus 220 and the image reception apparatus 230 are wired or wirelessly connected to each other.

The medical observation apparatus 210 images an imaging target and generates a medical image. The medical observation apparatus 210 is an apparatus having a function of capturing an image, such as an endoscope and a microscope, and can have a configuration similar to that of the medical observation apparatus 110 according to the first embodiment.

The image processing apparatus 220 performs image processing described below on the medical image output from the medical observation apparatus 210, and generates a presentation image. Further, the image processing apparatus 220 outputs the generated presentation image to the image reception apparatus 230.

The image processing apparatus 220 only needs to be an apparatus capable of performing image processing such as camera shake correction on a medical image, and can be an IP converter or a server (see FIG. 2).

The image reception apparatus 230 receives the presentation image output from the image processing apparatus 220. the image reception apparatus 230 is a display that displays a presentation image, a recorder that records a presentation image, an image management server, or the like, and can have a configuration similar to that of the image reception apparatus 130 according to the first embodiment.

[Regarding Configuration of Image Processing Apparatus]

Figure 18:
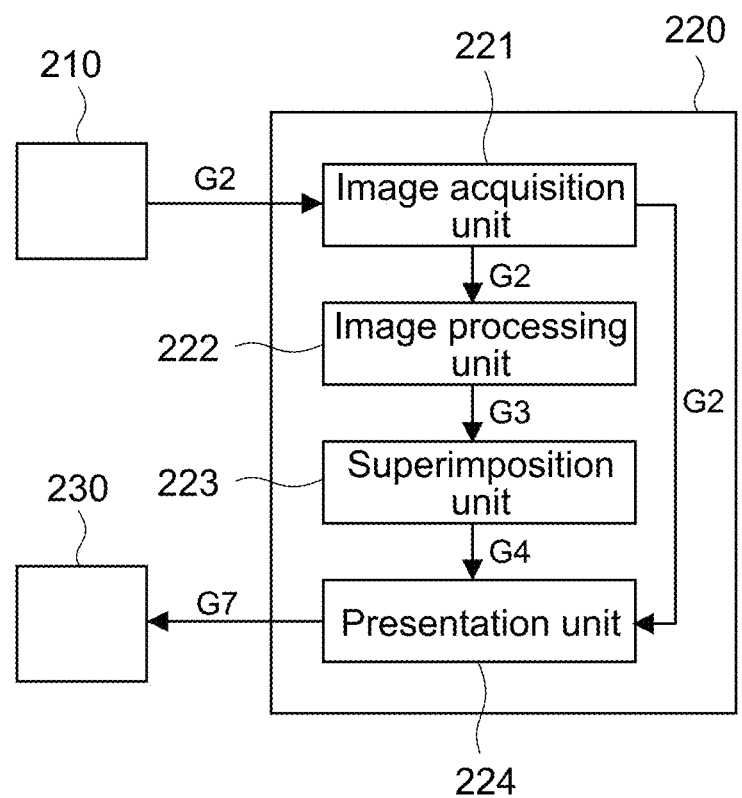
FIG. 18 is a block diagram showing a configuration of the image processing apparatus included in the medical image transmission system.

The configuration of the image processing apparatus 220 will be described. FIG. 18 is a schematic diagram showing a functional configuration of the image processing apparatus 220.

As shown in the figure, the image processing apparatus 220 includes an image acquisition unit 221, an image processing unit 222, a superimposition unit 223, and a presentation unit 224. These are functional configurations realized by the cooperation of software and hardware.

The configurations of the image acquisition unit 221, the image processing unit 222, and the superimposition unit 223 are respectively the same as those of the image acquisition unit 121, the image processing unit 122, and the superimposition unit 123 according to the first embodiment.

That is, the image acquisition unit 221 acquires the medical image G2 (see FIG. 4) from the medical observation apparatus 210, and supplies the acquired image to the image processing unit 222 and the presentation unit 224.

The image processing unit 222 applies image processing such as camera shake correction to the medical image G2, and generates the medical image G3 (see FIG. 5). The image processing unit 222 supplies the generated medical image G3 to the superimposition unit 223.

The superimposition unit 223 superimposes a superimposition image such as a digital mask on a predetermined area of the medical image G3 to generate the medical image G4 (see FIG. 6). The superimposition unit 223 supplies the generated medical image G4 to the presentation unit 224.

The presentation unit 224 presents information to a user on the basis of the additional information 174 that has been displayed on the optical mask area 173 before performing the image processing by the image processing unit 222. Specifically, the presentation unit 224 extracts an area including the additional information 174 in the medical image G2.

Figure 19:
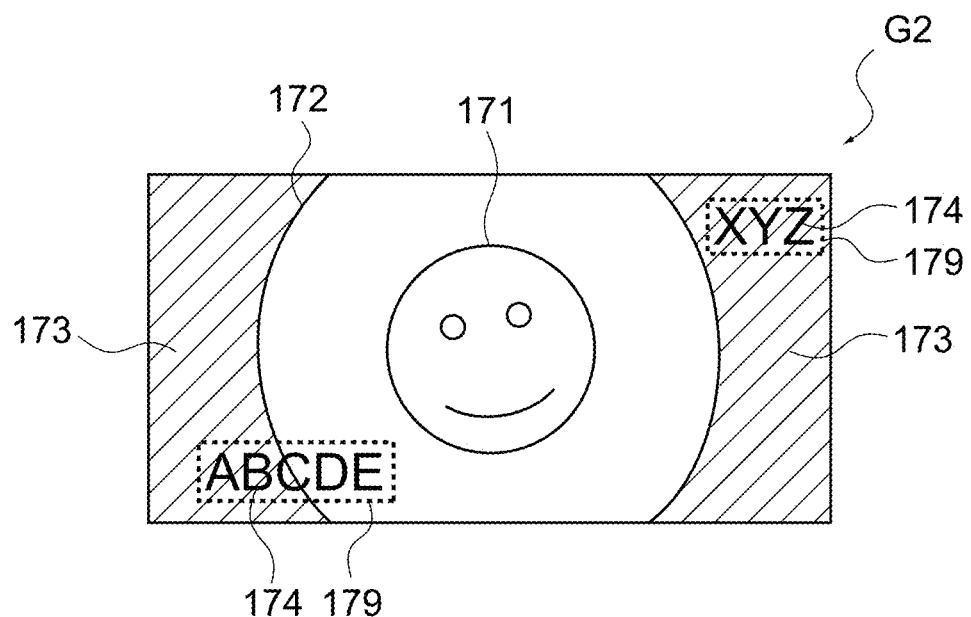
FIG. 19 is a schematic diagram showing how additional information is extracted by the presentation unit of the image processing apparatus included in the medical image transmission system.

FIG. 19 is a schematic diagram showing an area (hereinafter, additional information area) 179 including the additional information 174. As shown in the figure, the presentation unit 224 extracts, as the additional information area 179, the area in which the additional information 174 is present in the medical image G2.

The presentation unit 224 may extract the additional information area 179 by image recognition. Note that the shape of the additional information area 179 may be appropriately set in accordance with the shape of the additional information 174, such as a rectangular shape and an elliptical shape.

Figure 20:
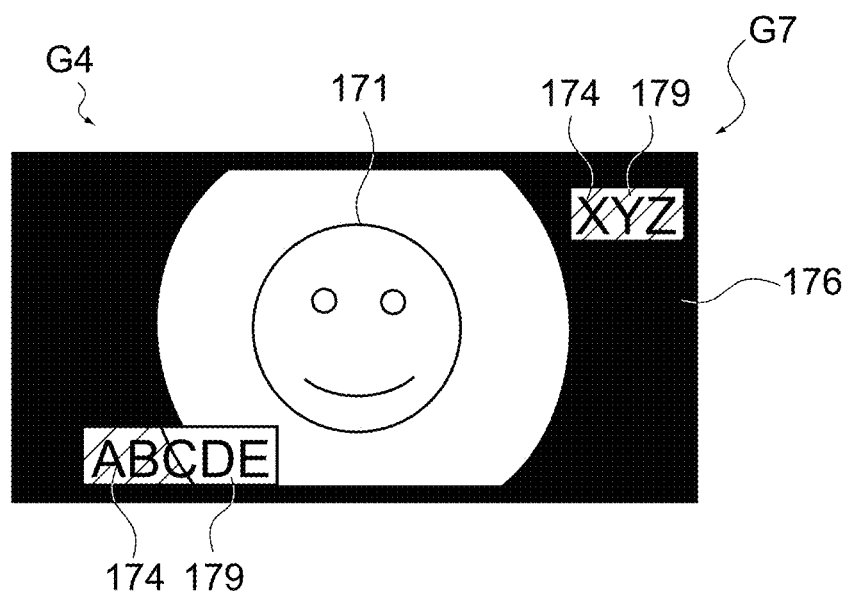
FIG. 20 is an example of a presentation image generated by the presentation unit of the image processing apparatus included in the medical image transmission system.

Further, the presentation unit 224 draws out the extracted additional information area 179 from the medical image G2, and superimposes the drawn area on the medical image G4 (see FIG. 6) to generate a presentation image. FIG. 20 is a diagram showing a presentation image G7 obtained by superimposing the additional information area 179 on the medical image G4.

As shown in FIG. 20, the presentation unit 224 disposes the additional information area 179 on the medical image G4 to generate the presentation image G7. The presentation unit 224 may dispose the additional information area 179 in the medical image G4 such that the positional coordinates of the additional information area 179 are the same as the positional coordinates of the additional information area 179 in the medical image G2.

Note that in the case where the presentation unit 224 cuts out only the additional information 174 from the medical image G2, the calculation load is large, but the calculation load can be suppressed by cutting out a certain area including the additional information 174 as the additional information area 179.

As a result, as shown in FIG. 20, the presentation image G7 is generated. The presentation unit 124 outputs the generated presentation image G7 to the image reception apparatus 230.

[Effects by Medical Image Transmission System]

As described above, in the transmission system 200, the image processing apparatus 220 performs various types of processing on the medical image G2 (see FIG. 4) output from the medical observation apparatus 210, generates the presentation image G7, and outputs the generated image to the image reception apparatus 230.

In the presentation image G7, image processing such as camera shake correction is performed on the image 171 and the digital mask 176 is superimposed on the periphery of the image 171. Therefore, the optical mask boundary 172, the additional information 174, and the periphery 175 are covered by the digital mask 176, and the visibility is prevented from being deteriorated due to the shaking motion thereof.

Further, the additional information area 179 extracted from the medical image G2 before image processing is superimposed in the presentation image G7, and the additional information 174 can be checked. The additional information 174 in the medical image G2 is excellent in visibility because shaking motion due to camera shake correction has not occurred. As a result, a user can refer to both the medical image on which image processing has been performed and additional information that is not affected by the image processing.

Further, since only one monitor is necessary to display the presentation image G7, the increase in cost and installation location can be reduced and it does not take time and effort for setting, as compared with the case where the medical image G2 and the medical image G3 are displayed on a plurality of monitors.

Note that also in this embodiment, the image processing performed by the image processing unit 222 is not limited to camera shake correction, and may be zooming as shown in FIG. 7 or rotation as shown in FIG. 8. Also in these cases, the visibility of the additional information 174 in the medical image G3 is affected by the image processing, but it is possible to improve the visibility of the additional information 174 by generating the presentation image G7.

The hardware configuration of the image processing apparatus 220 can be similar to that described in the first embodiment (see FIG. 16).

Third Embodiment

A medical image transmission system according to a third embodiment of the present technology will be described.

[Configuration of Medical Image Transmission System]

Figure 21:
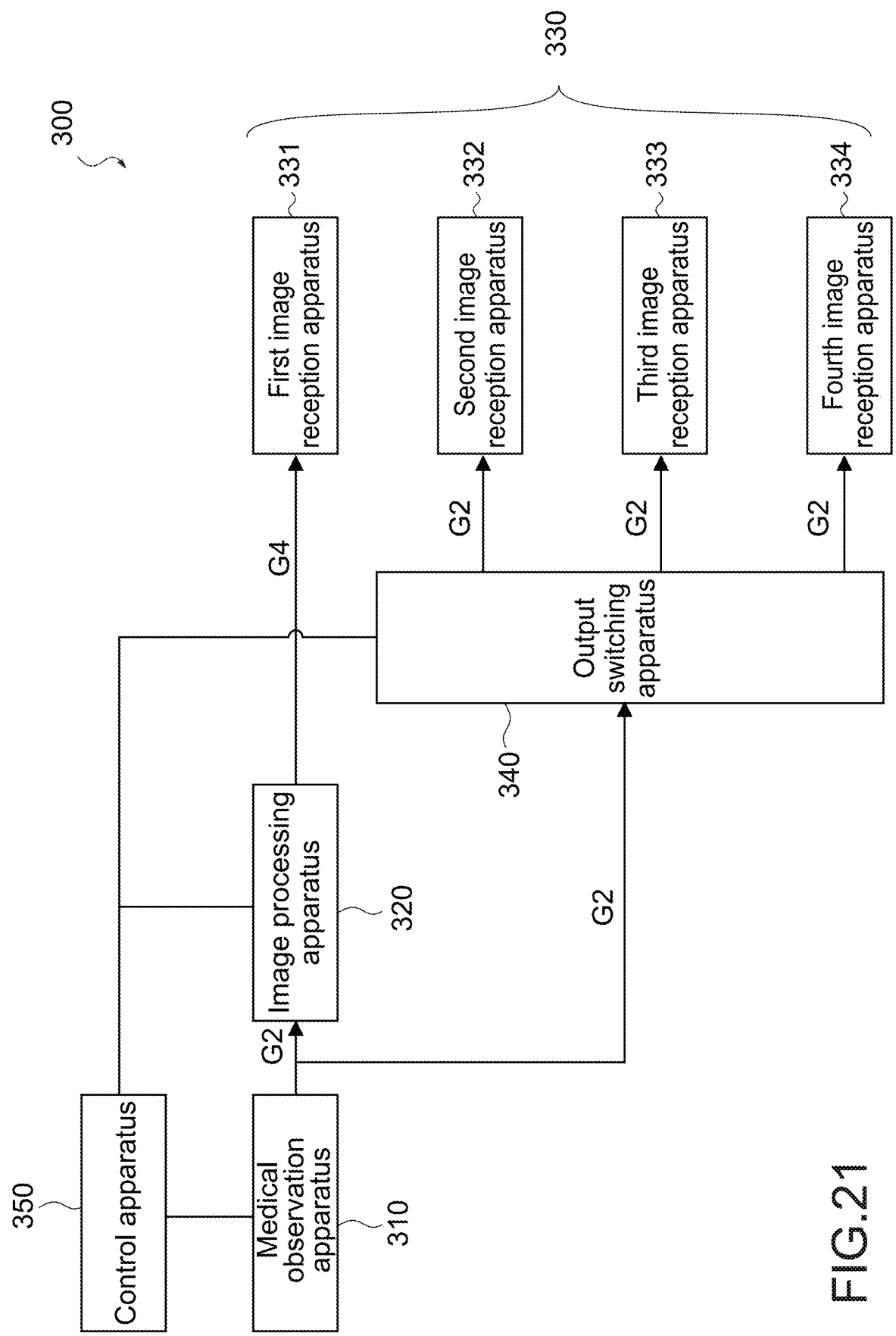
FIG. 21 is a block diagram showing a configuration of a medical image transmission system according to a third embodiment of the present technology.

FIG. 21 is a block diagram showing a configuration of a medical image transmission system 300 (hereinafter, the transmission system 300) according to this embodiment. As shown in the figure, the transmission system 300 includes a medical observation apparatus 310, an image processing apparatus 320, an image reception apparatus group 330, an output switching apparatus 340, and a control apparatus 350. The apparatuses are wired or wirelessly connected to each other.

The medical observation apparatus 310 images an imaging target and generates a medical image. The medical observation apparatus 310 is an apparatus having a function of capturing an image, such as an endoscope and a microscope, and can have a configuration similar to that of the medical observation apparatus 310 according to the first embodiment.

The image processing apparatus 320 performs image processing described below on the medical image output from the medical observation apparatus 310. The image processing apparatus 320 outputs the medical image on which the image processing has been performed to a first image reception apparatus 331 of the image reception apparatus group 330.

The image processing apparatus 320 only needs to be an apparatus capable of performing image processing such as camera shake correction on a medical image, and can be an IP converter or a server (see FIG. 2).

The image reception apparatus group 330 includes a plurality of image reception apparatuses. The image reception apparatus can be a monitor or the like that displays an image. In this embodiment, the image reception apparatus group 330 includes the first image reception apparatus 331, a second image reception apparatus 332, a third image reception apparatus 333, and a fourth image reception apparatus 334, but the image reception apparatus group 330 only needs to include three or more image reception apparatuses.

The output switching apparatus 340 acquires the medical image output from the medical observation apparatus 310, and switches the image reception apparatus that outputs the medical image. The output switching apparatus 340 only needs to switch the destination of the medical image, and the configuration thereof is not particularly limited.

The control apparatus 350 is connected to the medical observation apparatus 310, the image processing apparatus 320, and the output switching apparatus 340, and controls the respective apparatuses. In particular, the control apparatus 350 designates an image reception apparatus that outputs a medical image to the output switching apparatus 340. The control apparatus 350 only needs to be an apparatus capable of controlling the respective apparatuses, and is, for example, an information processing apparatus such as a system management server.

[Regarding Configuration of Image Processing Apparatus]

Figure 22:
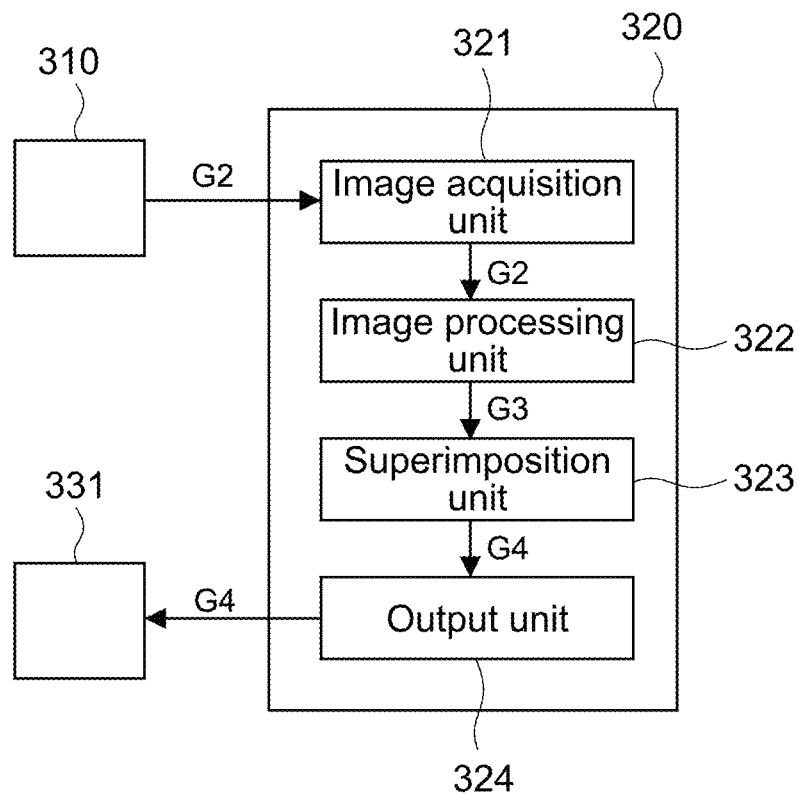
FIG. 22 is a block diagram showing a configuration of the image processing apparatus included in the medical image transmission system.

The configuration of the image processing apparatus 320 will be described. FIG. 22 is a schematic diagram showing a functional configuration of the image processing apparatus 320.

As shown in the figure, the image processing apparatus 320 includes an image acquisition unit 321, an image processing unit 322, a superimposition unit 323, and an output unit 324. These are functional configurations realized by the cooperation of software and hardware.

The configurations of the image acquisition unit 321, the image processing unit 322, and the superimposition unit 323 are the same as the image acquisition unit 321, the image processing unit 322, and the superimposition unit 323 according to the first embodiment.

That is, the image acquisition unit 321 acquires the medical image G2 (see FIG. 4) from the medical observation apparatus 310 and supplies the acquired image to the image processing unit 322.

The image processing unit 322 applies image processing such as camera shake correction to the medical image G2 to generate the medical image G3 (see FIG. 5). The image processing unit 322 supplies the generated medical image G3 to the superimposition unit 323.

The superimposition unit 323 superimposes a superimposition image such as a digital mask on a predetermined area of the medical image G3 to generate the medical image G4 (see FIG. 6). The superimposition unit 323 supplies the generated medical image G4 to the output unit 324.

The output unit 324 outputs the medical image G4 to the first image reception apparatus 331. As a result, the medical image G4 is displayed in the first image reception apparatus 331.

[Configuration of Control Apparatus]

Figure 23:
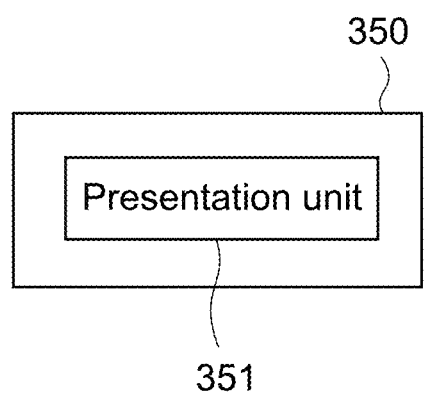
FIG. 23 is a block diagram showing a configuration of a control apparatus included in the medical image transmission system.

The configuration of the control apparatus 350 will be described. FIG. 23 is a schematic diagram showing a functional configuration of the control apparatus 350.

As shown in the figure, the control apparatus 350 includes a presentation unit 351. The presentation unit 351 presents information to a user on the basis of the additional information 174 that has been displayed on the optical mask area 173 before performing the image processing by the image processing unit 322.

Specifically, the presentation unit 351 controls the image processing apparatus 320 to output the medical image G4 to the first image reception apparatus 331.

Further, the presentation unit 351 selects one of the second image reception apparatus 332, the third image reception apparatus 333, and the fourth image reception apparatus 341, and controls the output switching apparatus 340 to output the medical image G2 to the selected image reception apparatus.

At this time, the presentation unit 351 may select an image reception apparatus adjacent to the first image reception apparatus 331, of the second image reception apparatus 332, the third image reception apparatus 333, and the fourth image reception apparatus 341.

[Operation of Medical Image Transmission System]

The transmission system 300 having the above-mentioned configuration operates as follows.

First, the control apparatus 350 controls the medical observation apparatus 310 to transmit the medical image G2 to the image processing apparatus 320.

Further, the control apparatus 350 controls the image processing apparatus 320 to execute image processing such as camera shake correction. As a result, image processing is executed by the image processing apparatus 320, and the medical image G4 (see FIG. 6) is generated. The medical image G4 is output from the image processing apparatus 320 to the first image reception apparatus 331.

Subsequently, the control apparatus 350 selects an image reception apparatus adjacent to the first image reception apparatus 331, of the second image reception apparatus 332, the third image reception apparatus 333, and the fourth image reception apparatus 341.

The control apparatus 350 notifies the output switching apparatus 340 of the selected image reception apparatus. The output switching apparatus 340 outputs, to the image reception apparatus that is the target of the notification from the control apparatus 350, the medical image G2 output from the medical observation apparatus 310.

As a result, the medical image G4 on which image processing has been performed is displayed on the first image reception apparatus 331, and the medical image G2 output from the medical observation apparatus 310 is displayed on an image reception apparatus adjacent to the first image reception apparatus 331.

Note that in the case where an image reception apparatus adjacent to the first image reception apparatus 311 is not present, the control apparatus 350 may control the image processing apparatus 320 to display an alert with a character or icon on the first image reception apparatus 311 or reproduce an alert sound.

[Effects by Medical Image Transmission System]

As described above, in the transmission system 300, the image processing apparatus 320 performs various types of processing on the medical image G2 (see FIG. 4) output from the medical observation apparatus 310, generates the medical image G4, and outputs the generated image to the first image reception apparatus 331.

In the medical image G4, image processing such as camera shake correction is performed on the image 171 and the digital mask 176 is superimposed on the periphery of the image 171. Therefore, the optical mask boundary 172, the additional information 174, and the periphery 175 are covered by the digital mask 176, and the visibility is prevented from being deteriorated due to the shaking motion thereof.

Further, in the transmission system 300, the medical image G2 output from the medical observation apparatus 310 is output to an image reception apparatus adjacent to the first image reception apparatus 331. The additional information 174 in the medical image G2 is excellent in visibility because shaking motion due to camera shake correction has not occurred. As a result, a user can refer to both the medical image on which image processing has been performed and additional information that is not affected by the image processing.

Note that also in this embodiment, the image processing performed by the image processing unit 322 is not limited to camera shake correction, and may be zooming as shown in FIG. 7 or rotation as shown in FIG. 8. Also in these cases, the visibility of the additional information 174 in the medical image G3 is affected by the image processing, but it is possible to improve the visibility of the additional information 174 by displaying the medical image G2 in another image reception apparatus.

The hardware configuration of the image processing apparatus 320 can be similar to that described in the first embodiment (see FIG. 16). Further, also the hardware configuration of the control apparatus 350 can be similar to that described in the first embodiment (see FIG. 16).

Note that although a digital mask is superimposed as a superimposition unit in the above-mentioned first to third embodiments, it only needs to superimpose an image that makes the additional information that has been displayed in a predetermined area invisible or difficult to visually recognize for a user. For example, a configuration in which electronic zooming is performed on a medical image and a zoom image is superimposed on the medical image and displayed, and then, information is presented to a user on the basis of the additional information that has been displayed on the original medical image may be employed. At this time, as superimposing a zoom image on the medical image, a zoom image may be displayed instead of displaying the medical image.

Note that the present technology may also take the following configurations.

(1) A medical image transmission system, including:

an image acquisition unit that acquires a medical image generated by a medical observation apparatus;

an image processing unit that applies predetermined image processing to the medical image;

a superimposition unit that superimposes a superimposition image on a predetermined area of the medical image; and a presentation unit that presents information to a user on a basis of additional information that has been displayed in the predetermined area before executing the predetermined image processing.

(2) The medical image transmission system according to (1) above, in which the superimposition image is a digital mask that covers a part of the medical image on which the predetermined image processing has been performed.

(3) The medical image transmission system according to (1) or (2) above, in which the presentation unit generates a presentation image, the medical image on which the superimposition image has been superimposed and the medical image generated by the medical observation apparatus being respectively disposed as a main image and a sub-image in a picture-in-picture manner in the presentation image.

(4) The medical image transmission system according to (3) above, in which
the superimposition unit superimpose, upon receiving a predetermined operation input, a superimposition image on the predetermined area, and
the presentation unit disposes the sub-image upon receiving the operation input.
(5) The medical image transmission system according to (3) or (4) above, in which
the presentation unit adjusts an image size of the sub-image in accordance with a size of the digital mask.
(6) The medical image transmission system according to any one of (3) to (5) above, in which
the image processing unit offsets the medical image obtained by performing the predetermined image processing on the medical image generated by the medical observation apparatus.
(7) The medical image transmission system according to any one of (3) to (6) above, in which
the presentation unit disposes a display item indicating a range of the digital mask on the sub-image.
(8) The medical image transmission system according to any one of (3) to (7) above, in which
the presentation unit extracts the additional information from the sub-image and performs processing of emphasizing the additional information in the sub-image.
(9) The medical image transmission system according to any one of (2) to (8) above, in which
the presentation unit is capable of switching between a first state and a second state, a presentation image in which the medical image on which the superimposition image has been superimposed and the medical image generated by the medical observation apparatus being respectively disposed as a main image and a sub-image in a picture-in-picture manner being generated in the first state, a presentation image in which the medical image generated by the medical observation apparatus and the medical image on which the superimposition image has been superimposed being respectively disposed as a main image and a sub-image in a picture-in-picture manner being generated in the second state.
(10) The medical image transmission system according to any one of (1) to (9) above, in which
the predetermined image processing is camera shake correction.
(11) The medical image transmission system according to any one of (1) to (9) above, in which
the predetermined image processing is zooming of the medical image.
(12) The medical image transmission system according to any one of (1) to (9) above, in which
the predetermined image processing is rotation of the medical image.
(13) The medical image transmission system according to (1) above, in which
the presentation unit cuts out an additional information area that is an area in which the additional information is present from the medical image generated by the medical observation apparatus, and disposes the additional information area on the medical image on which the superimposition image has been superimposed.
(14) The medical image transmission system according to (1) above, further including:
an image processing apparatus that includes the image acquisition unit, the image processing unit, and the superimposition unit;
an output switching apparatus that switches an image reception apparatus that outputs the medical image generated by the medical observation apparatus, of a plurality of image reception apparatuses; and
and a control apparatus that includes the presentation unit, in which
the presentation unit causes a first image reception apparatus to output the medical image on which the superimposition image has been superimposed by the superimposition unit to the image processing apparatus, and causes a second image reception apparatus adjacent to the first image reception apparatus to output the medical image generated by the medical observation apparatus to the output switching apparatus.
(15) A medical image processing apparatus, including:
an image acquisition unit that acquires a medical image generated by a medical observation apparatus;
an image processing unit that applies predetermined image processing to the medical image;
a superimposition unit that superimposes a superimposition image on a predetermined area of the medical image; and
a presentation unit that generates a presentation image including a medical image on which a superimposition image has been superimposed by the superimposition unit and additional information that has been displayed in the predetermined area before executing the predetermined image processing.
(16) A medical image transmission method, including:
acquiring, by an image acquisition unit, a medical image generated by a medical observation apparatus;
applying, by an image processing unit, predetermined image processing to the medical image;
superimposing, by a superimposition unit, a superimposition image on a predetermined area of the medical image; and
presenting, by a presentation unit, information to a user on a basis of additional information that has been displayed in the predetermined area before executing the predetermined image processing.

REFERENCE SIGNS LIST 100, 200, 300 medical image transmission system
110, 210, 310 medical observation apparatus
120, 220, 320 image processing apparatus
121, 221, 321 image acquisition unit
122, 222, 322 image processing unit
123, 223, 323 superimposition unit
124, 224, 351 presentation unit
130, 230 image reception apparatus
330 image reception apparatus group
340 output switching apparatus
350 control apparatus

The invention claimed is:
1. A medical image transmission system, comprising:
control circuitry configured to:
acquire a medical image generated by a medical observation apparatus;
apply predetermined image processing to the medical image; and
superimpose a superimposition image on a predetermined area of the medical image; and
display circuitry configured to present information to a user on a basis of additional information that has been displayed in the predetermined area. before executing the predetermined image processing, wherein the superimposition image is a digital mask that covers a part of the medical image on which the predetermined image processing has been performed.

2. The medical image transmission system according to claim 1, wherein
the display circuitry is further configured to generate a presentation image, the medical image on which the superimposition image has been superimposed and the medical image generated by the medical observation apparatus being respectively disposed as a main image and a sub-image in a picture-in-picture manner in the presentation image.

3. The medical image transmission system according to claim 2, wherein:
the control circuitry is further configured to superimpose, upon receiving a predetermined operation input, the superimposition image on the predetermined area, and
the display circuitry is further configured to dispose the sub-image upon receiving the operation input.

4. The medical image transmission system according to claim 2, wherein
the display circuitry is further configured to adjust an image size of the sub-image in accordance with a size of the digital mask.

5. The medical image transmission system according to claim 2, wherein
the circuitry is further configured to offset the medical image obtained by performing the predetermined image processing on the medical image generated by the medical observation apparatus.

6. The medical image transmission system according to claim 2, wherein
the display circuitry is further configured to dispose a display item indicating a range of the digital mask on the sub-image.

7. The medical image transmission system according to claim 2, wherein
the display circuitry is further configured to extract the additional information from the sub-image and performs processing of emphasizing the additional information in the sub-image.

8. The medical image transmission system according to claim 1, wherein
the display circuitry is further configured to switch between a first state and a second state, a presentation image in which the medical image on which the superimposition image has been superimposed and the medical image generated by the medical observation apparatus being respectively disposed as a main image and a sub-image in a picture-in-picture manner being generated in the first state, a presentation image in which the medical image generated by the medical observation apparatus and the medical image on which the superimposition image has been superimposed being respectively disposed as a main image and a sub-image in a picture-in-picture manner being generated in the second state.

9. The medical image transmission system according to claim 1, wherein
the predetermined image processing is camera shake correction.

10. The medical image transmission system according to claim 1, wherein
the predetermined image processing is zooming of the medical image.

11. The medical image transmission system according to claim 1, wherein
the predetermined image processing is rotation of the medical image.

12. The medical image transmission system according to claim 1, wherein
the display circuitry is further configured to cut out an additional information area that is an area in which the additional information is present from the medical image generated by the medical observation apparatus, and disposes the additional information area on the medical image on which the superimposition image has been superimposed.

13. The medical image transmission system according to claim 1, further comprising:
an image processing apparatus that includes the control circuitry:
an output switching apparatus that switches an image reception apparatus that outputs the medical image generated by the medical observation apparatus, of a plurality of image reception apparatuses; and
a control apparatus that includes the display circuitry, wherein
the display circuitry is configured to cause a first image reception apparatus to output the medical image on which the superimposition image has been superimposed by the control circuitry to the image processing apparatus, and causes a second image reception apparatus adjacent to the first image reception apparatus to output the medical image generated by the medical observation apparatus to the output switching apparatus.

14. A medical image processing apparatus, comprising:
control circuitry configured to:
acquire a medical image generated by a medical observation apparatus;
apply predetermined image processing to the medical image; and
superimpose a superimposition image on a predetermined area of the medical image; and
a display circuitry configured to generate a. presentation image including a medical image on which the superimposition image has been superimposed by the control circuitry and additional information that has been displayed in the predetermined area before executing the predetermined image processing,
wherein the superimposition image is a digital mask that covers a part of the medical image on which the predetermined image processing has been performed.

15. A medical image transmission method performed by a medical image processing apparatus, the medical image transmission method comprising:
acquiring, by the medical image processing apparatus, a medical image generated by a medical observation apparatus;
applying, by the medical image processing apparatus, predetermined image processing to the medical image;
superimposing, by the medical imaue processing apparatus, a superimposition image on a predetermined area of the medical image; and
presenting, by the medical image processing apparatus, information to a user on a basis of additional information that has been displayed in the predetermined area before executing the predetermined image processing, wherein the superimposition image is a digital mask that covers apart of the medical image on which the predetermined image processing has been performed.

* * * * *